United States Patent [19]
Carrico, Jr. et al.

[11] Patent Number: 5,356,814
[45] Date of Patent: Oct. 18, 1994

[54] DISAGGREGATION DEVICE FOR CYTOLOGICAL SPECIMENS

[75] Inventors: Charles L. Carrico, Jr.; William A. Fox, both of Burlington; James W. Geyer; Ernest A. Knesel, Jr., both of Greensboro, all of N.C.

[73] Assignee: Hoffmann-La Roche Inc., Nutley, N.J.

[21] Appl. No.: 112,003

[22] Filed: Aug. 30, 1993

Related U.S. Application Data

[63] Continuation-in-part of Ser. No. 953,035, Sep. 29, 1992.

[51] Int. Cl.⁵ ............................... C12M 3/02
[52] U.S. Cl. ................... 435/286; 435/284; 435/803; 422/99; 422/101; 422/102
[58] Field of Search .............. 422/101, 99, 102, 58; 435/284, 286, 803, 285

[56] References Cited

U.S. PATENT DOCUMENTS

| | | | |
|---|---|---|---|
| 3,941,317 | 3/1976 | Kanor | 241/21 |
| 4,350,768 | 9/1982 | Tihon et al. | 435/241 |
| 4,783,318 | 11/1988 | Lapakko | 422/101 |
| 4,816,161 | 3/1989 | Olness et al. | 210/638 |
| 4,904,450 | 2/1990 | Floyd | 422/113 |
| 5,124,041 | 6/1992 | Sheer et al. | 210/641 |
| 5,160,413 | 11/1992 | Allisson | 203/35 |
| 5,208,161 | 5/1993 | Saunders et al. | 435/286 |

FOREIGN PATENT DOCUMENTS 1270511  8/1958  France.

OTHER PUBLICATIONS

Translation of FR 1 270 511.

*Primary Examiner*—James C. Housel
*Assistant Examiner*—Lien Tran
*Attorney, Agent, or Firm*—George M. Gould; George W. Johnston; John P. Parise

[57] ABSTRACT

A device for disaggregating cytological material includes a cylindrical body and a plurality of shear plates at least one of which is located at the bottom end of the cylindrical body. The shear plates have a plurality of holes or slots formed therein which disaggregate the cellular sample and permit the passage of single cells and small cell clusters into a chamber defined by the cylindrical body.

10 Claims, 10 Drawing Sheets

DISAGGREGATION DEVICE FOR CYTOLOGICAL SPECIMENS

CROSS-REFERENCE TO PRIOR APPLICATIONS

This application is a continuation-in-part of Ser. No. 07/953,035, filed Sep. 29, 1992 pending.

FIELD OF THE INVENTION

The invention pertains to a device which disaggregates cytological material for specimen analysis.

BACKGROUND OF THE INVENTION

Usually the cell suspensions received from doctors' clinics contain sample cells which have become aggregated or clumped together. To properly analyze this material, it is important to have a representative sample of single cells present on the microscope slide, with a minimum number of aggregated cell clumps. This is especially true for automated slide analysis.

A prerequisite for the screening of cytological material by an automated image analysis system is a reproducible and practical method for preparing smears of disaggregated cell suspensions. Many procedures have been described, for example, syringing, shaking, ultrasonic methods, and chemical methods, e.g., trypsinizing.

Of these, the most widely used is the syringing technique. This technique involves the use of a syringe typically having a 19-gauge needle. The cell suspension is drawn up into the syringe and then quickly expelled. The turbulent flow from the syringe shears and breaks up cell aggregates. This process is repeated many times, and can be done manually or automatically with a peristaltic pump. The difficulty with these techniques is that although effective, they are limited since they are labor-intensive and/or very time consuming.

SUMMARY OF THE INVENTION

The invention pertains to a device for disaggregating cytological material contained within a sample vial and permitting the flow of the material to a tube. This device comprises an elongated hollow body configured to be slidably inserted into the sample vial, sealing means for forming a liquid-impervious seal between the sample vial and the device when the device is inserted into the sample vial, a plurality of shear plates, and means for securing the top end of the body to a tube to permit disaggregated cytological material to flow from the body into the tube. The body has a top end, a bottom end and sides. At least one of the shear plates is disposed across the bottom end of the body. Each shear plate defines a plurality of holes of predetermined size effective to disaggregate the cytological material and to permit the disaggregated cytological material to traverse the shear plates and enter the body when the body is inserted into the sample vial.

The bottom end portion of the body includes at least one shear plate preferably oriented substantially perpendicular to the longitudinal axis of the hollow body. The area located above the shear plate and confined within the sides of the hollow body defines a chamber for fluid containment. During use, the device is inserted into a specimen sample vial, so that the sealing means, such as an O-ring, fit snugly between the exterior surface of the device and the interior surface of the sample vial. This seal prevents the cell suspension from exiting into the area between the exterior wall of the device and the interior wall of the vial.

When the device is pushed into the sample vial, the cell suspension is forced through the shear plates and into the interior of the hollow body (chamber 11). For additional disaggregation, the device may be alternately withdrawn from and inserted into the vial to create a vacuum effect in the vial which volleys the cytological material between the chamber and the vial. This process may be repeated depending on the degree of disaggregation required. The disaggregated suspension within the chamber is then ready for subsequent use.

The device may also include a connector fitting to removably connect the top end of the device to a hose or other drainage tube. The device may be inverted together with the sample vial attached at the bottom end of the body. This inversion drains the disaggregated suspension from the chamber into a centrifuge tube or any other desired container via an opening in the top of the device. Preferably, a curved drainage tube is provided. The curved drainage tube contacts the inner surface of a centrifuge tube to permit a gentle flow of the disaggregated material, so as not to disturb a density gradient within the tube. To facilitate the inverted drainage, its useful to have a small hole in the body portion to permit an influx of air into the chamber without permitting an egress of liquid.

DETAILED DESCRIPTION OF THE INVENTION

The invention will now be described in terms of its preferred embodiments. These embodiments are set forth to aid in the understanding of the invention, but are not to be construed as limiting.

The invention is directed to a device for disaggregating cytological material. The term "disaggregating"

refers to the separation of cells from large cell clusters into single cells or smaller clusters of cells.

Figure 1:
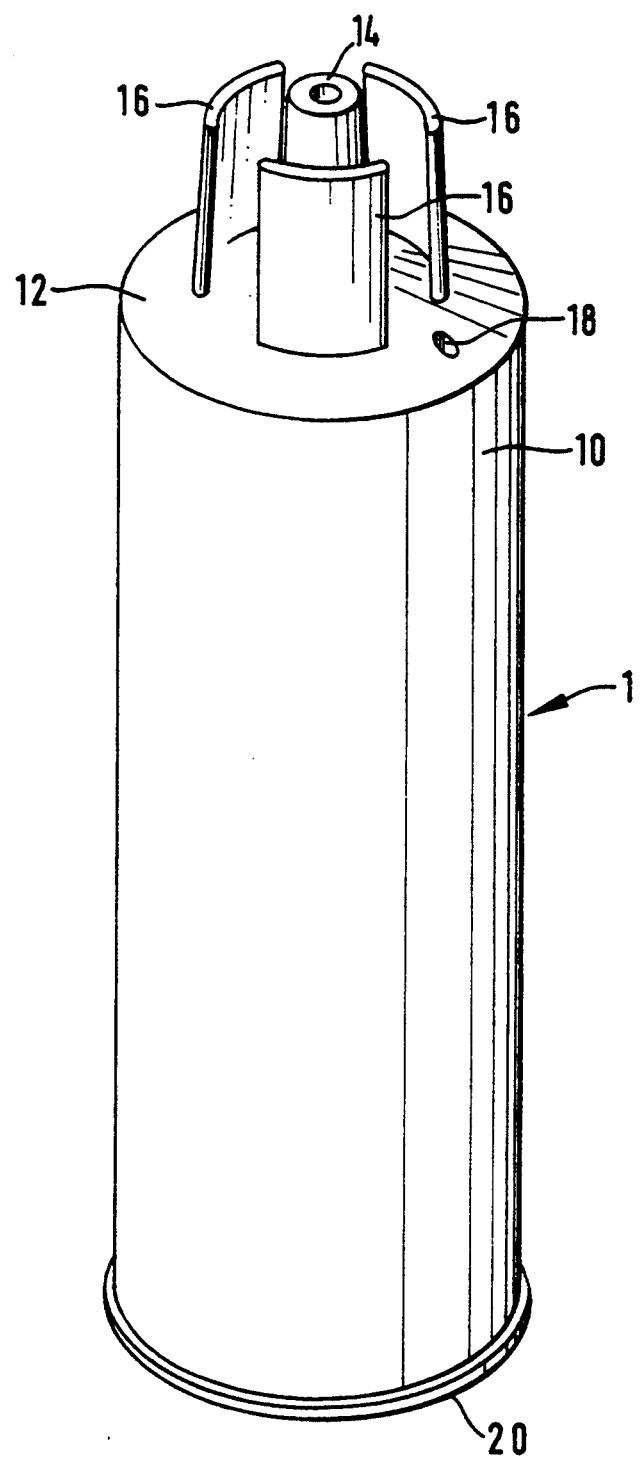
FIG. 1 is a top perspective view of a preferred embodiment of the invention.
Figure 2:
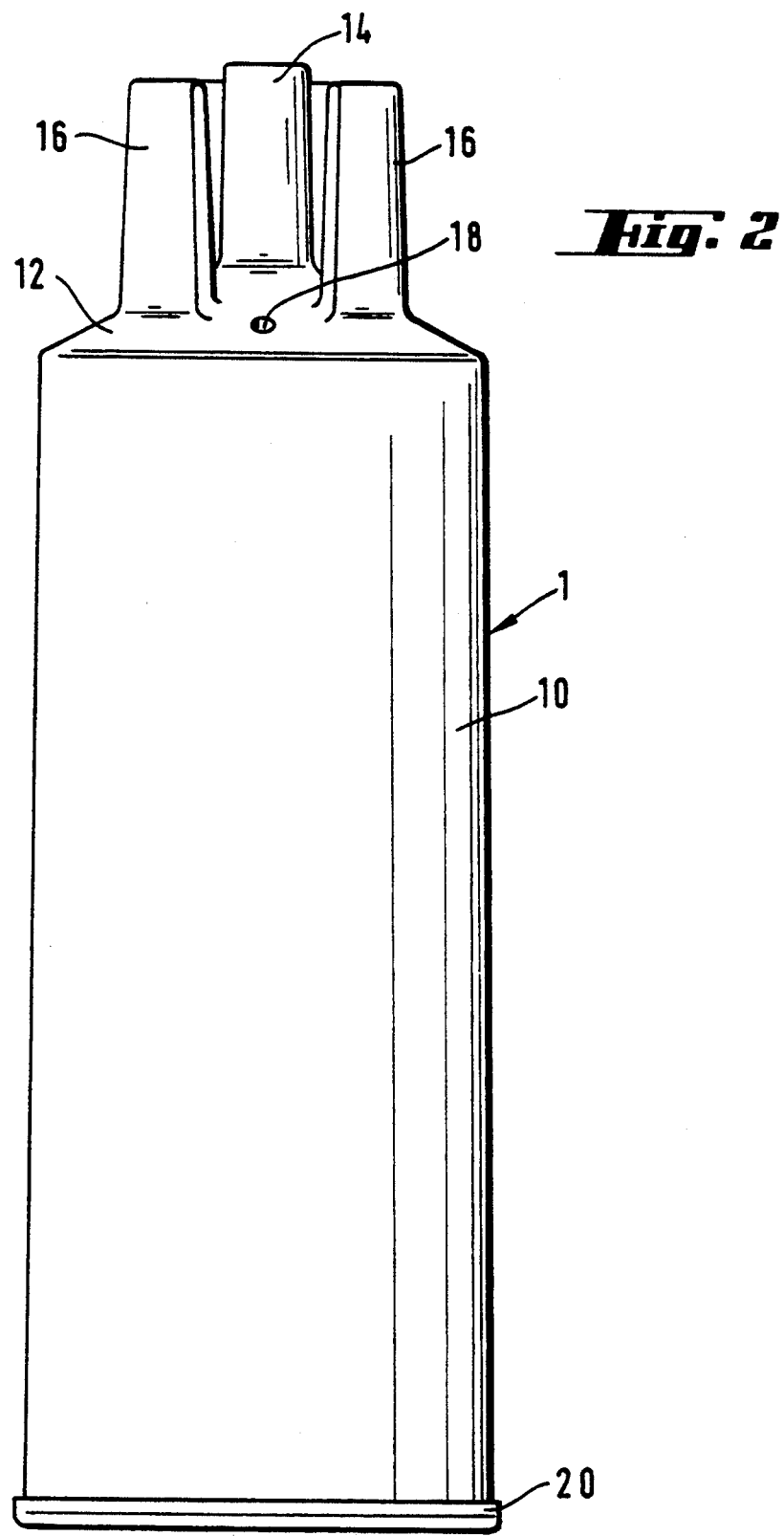
FIG. 2 is a side view of a preferred embodiment of the invention.

Referring to FIG. 2, device 1 is shown with body portion 10 which preferably is an elongated hollow member similar to the body of a syringe. More preferably, body 10 is predominantly configured as a hollow cylinder. Body 10 may be constructed as single unit, or may be made of multiple pieces which are assembled. The top end of body 10 may be open to the atmosphere, or preferably, may be formed with a tapered portion 12 as shown in FIG. 2. Tapered portion 12 leads to the connector member 14 which may be used to removably connect the device 1 to a hose or other means for drainage of disaggregated cell suspension located in chamber 11. Preferably, the means for drainage includes a curved tube 19 configured and dimensioned to contact the inside wall of a centrifuge tube 17 to allow gentle layering of the cell suspension onto a density gradient.

Connector member 14 may be of any type which provides for quick removal, e.g. interlocking, or a simple male-female type connection, as shown. Also located on tapered portion 12 is securing means 16 which permits device 1 to be inverted and secured to a receptacle, such as a test tube or centrifuge tube (shown as 17) during drainage. Securing means 16 is designed to fit snugly against the interior wall of the receptacle. Alternatively, securing means 16 may be configured to fit snugly around the exterior wall of the receptacle to steady inverted device 1 in place during drainage. Securing means 16 shown in FIG. 2 is a preferred embodiment of the invention and is designed to bias against the interior wall of the receptacle. Securing means 16, as shown, comprises three flanges equidistantly disposed about connector means 14. Securing means 16 could also take the form of a single flange which completely encircles the connector means 14. Any type of securing means which can securely hold the inverted device 1 to a receptacle opening is suitable for use in the invention.

Air vent 18 is provided through the wall of the device to permit the passage of air therethrough during either the filling of the device with cell suspension or during the drainage of the cell suspension from the device. The location of the air vent 18 is a matter of design choice.

FIG. 2 also shows sealing member 20 located at the bottom end of the device. Sealing member 20 is typically an annular ring-shaped protrusion (similar in effect to an O-ring) which provides a substantially liquid-impervious seal around the exterior of the device when the device is inserted bottom end first into a sample vial. Sealing member 20 preferably is integrally formed with first shear plate member 24, although sealing member 20 could alternatively or additionally be integrally formed with cylindrical body 10. Alternatively, sealing member 20 may be a separate O-ring circumscribing body 10. To aid in insertion, sealing member 20 may be lubricated, such as with silicone.

Figure 3:
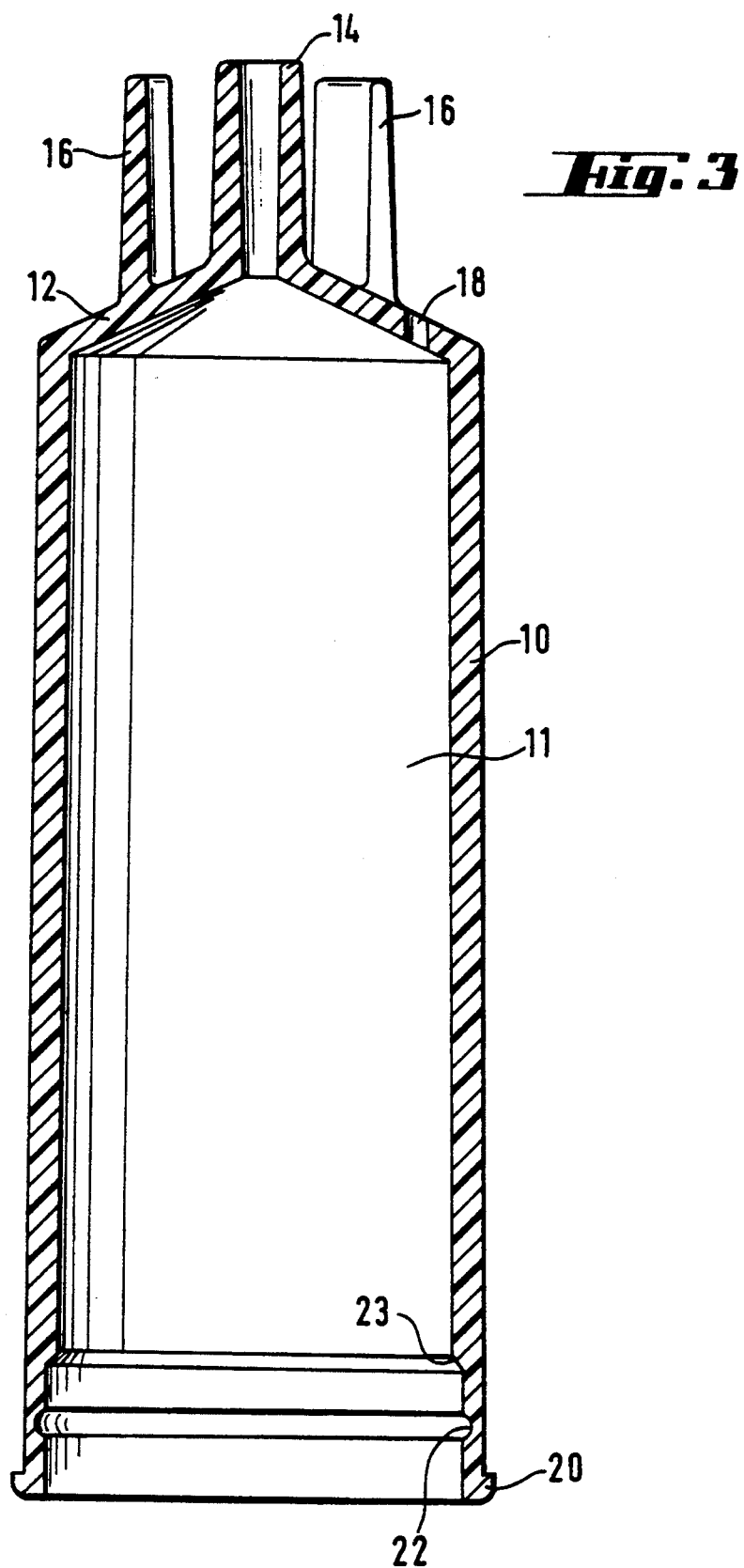
FIG. 3 is a cross-sectional view of the device of FIG. 1.

FIG. 3 shows a cross-sectional view of the device of FIG. 2. With the exception of annular groove 22, all elements illustrated in FIG. 3 are also present in FIG. 2 and have been previously described and explained. Annular groove 22, shown in FIG. 3 proximate to the bottom end of body 10, receives annular ring 30 of a first shear plate member 24 (shown in FIGS. 4 to 6).

Figure 4:
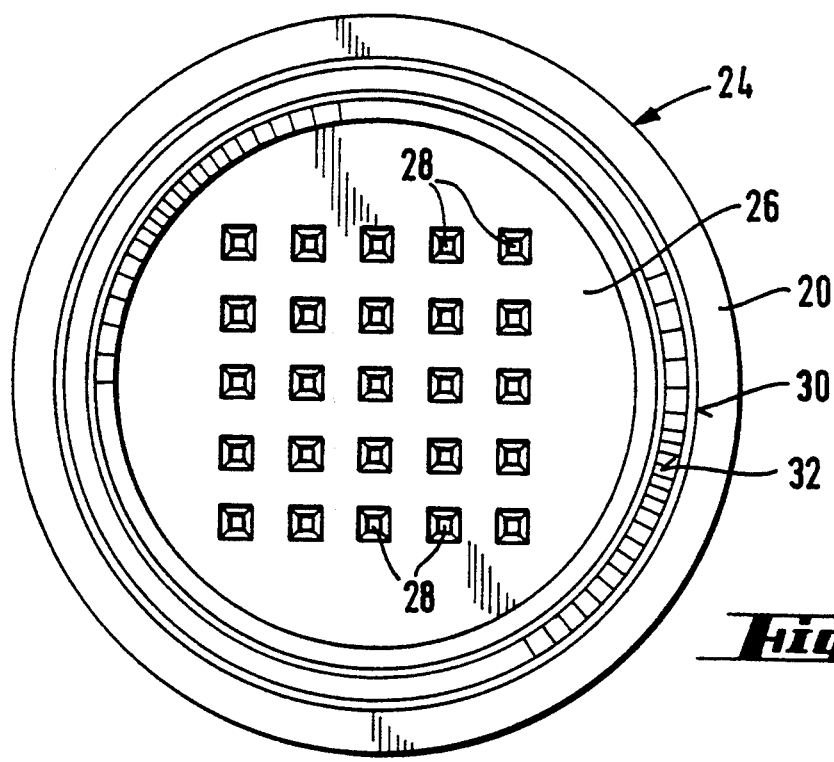
FIG. 4 is a top view of a first shear plate.
Figure 5:
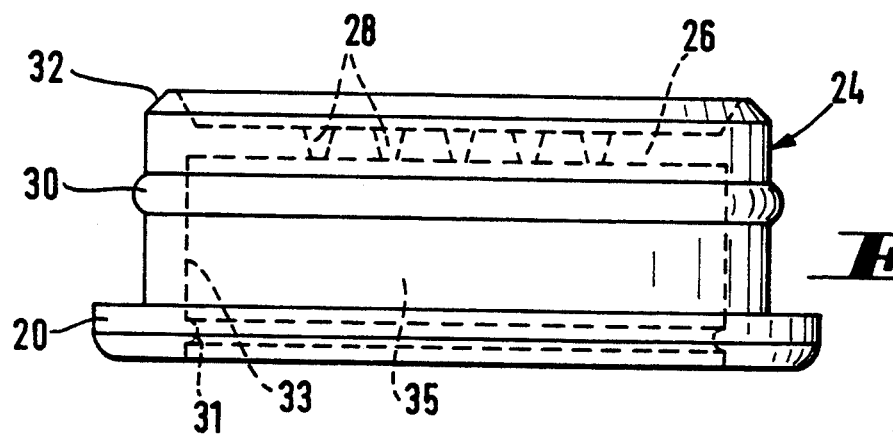
FIG. 5 is a side view of the assembly for the first shear plate shown in FIG. 4.
Figure 6:
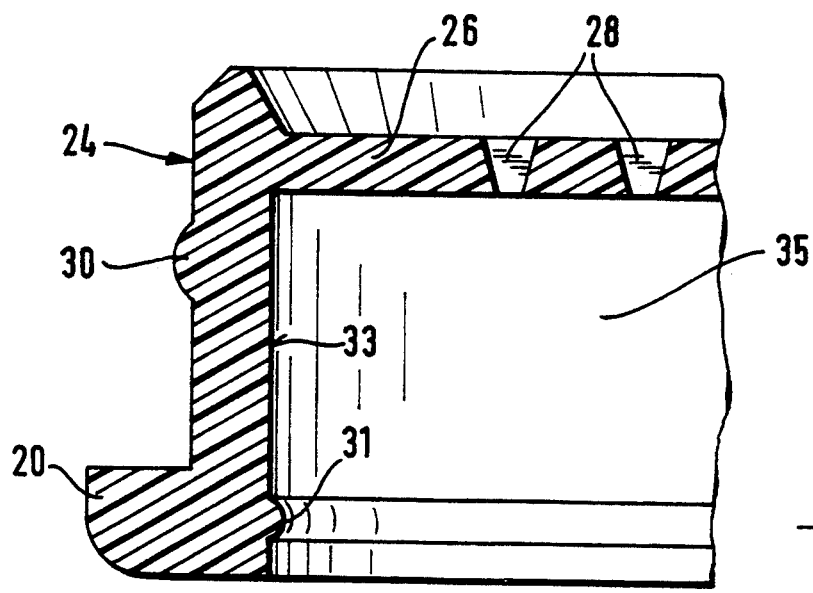
FIG. 6 shows a partial cross-sectional view of the first shear plate.

First shear plate member 24 is shown in FIGS. 4 to 6. In a preferred embodiment, first shear plate member 24 spans the entire cross-section of the body 10. Shear plate member 24 preferably includes annular ring 30 disposed around its exterior to connect with annular groove 22, providing an interlocking mechanism between first shear plate member 24 and cylindrical body 10. Any type of interlocking means may be used which removably connects first shear plate member 24 to cylindrical body 10. Indeed, the interlocking mechanism may take the form of threaded grooves, a mechanical interface, or the like. As shown in FIG. 6, an additional annular ring 31 may be disposed or formed on inner wall 33 of shear plate member 24.

Figure 8:
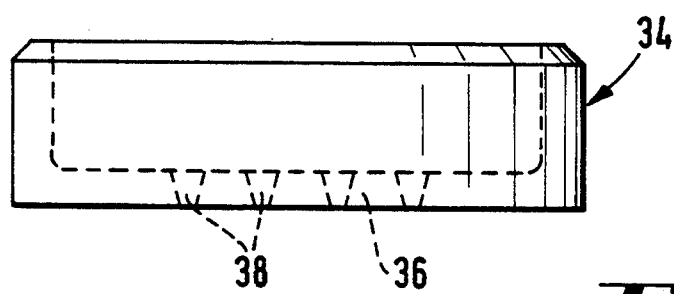
FIG. 8 is a side view of the assembly for the second shear plate shown in FIG. 7.
Figure 9:
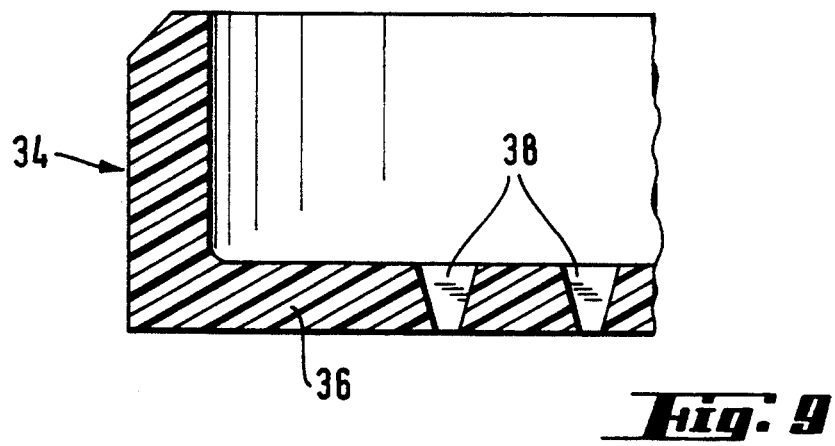
FIG. 9 shows a partial cross-sectional view of the second shear plate.

Annular ring 31 is designed to provide an interlocking mechanism with an additional or second shear plate member 34, which in a preferred embodiment, is inserted within opening 35. The positioning of first shear plate 26 is shown in FIG. 6 at an upper location of the member 34, generally perpendicular to the longitudinal axis of cylindrical body 10. However, the invention also encompasses shear plate 26 placed at a location anywhere along the longitudinal axis of member 24. The second shear plate is shown in detail in FIGS. 7 to 9.

First shear plate member 24 includes shear plate 26 which comprises a plurality of holes or slots 28 formed therethrough for permitting passage of cytological material. The holes shown in FIG. 4 are square in shape, however, holes of any shape may be used. Preferably, the holes are about 0.030 inch (760 micrometers) by 0.030 (760 micrometers) inch squares at their bottom edge. However, hole size in theory may vary from slightly larger than the cells to be disaggreated to a hundred times or more the cell size. Preferred diameter ranges for round holes are from about 300 micrometers to about 1,500 micrometers, more preferably from about 500 micrometers to about 1,000 micrometers, and most preferably about 800 micrometers.

To make the shear plates act like a perforated plane, the holes are typically tapered outward as they upwardly traverse the shear plate. The currently preferred outward taper is 15° relative to a plane drawn parallel to the longitudinal axis and tangential to the edge of the hole. Thus, the opening on the top of a shear plate is preferably larger than that on the bottom. The size and number and size of holes 28 and 38 may be optimized by one of ordinary skill in the art for the type of tissue being disaggregated and the level of disaggregation desired. First shear plate member 24 includes an angled edge 32 located at its upper most end. When shear plate member 24 is inserted into the bottom end of cylindrical body 10, the angled edge 32 abuts the edge 23 within the cylindrical body ensuring a proper fit.

Figure 7:
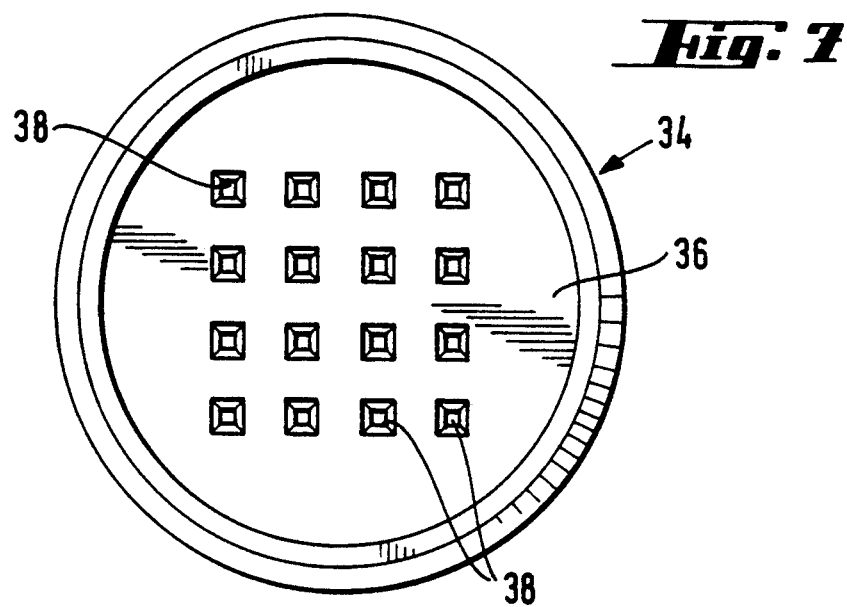
FIG. 7 is a top view of a second shear plate.

FIG. 7 shows second shear plate member 34 including shear plate 36 which defines a plurality of holes or slots 38. In a similar manner to first shear plate 26, second shear plate 36 preferably covers the entire cross-section of the hollow body. Holes 38 can be of any size which permit passage of cytological material and promote the shearing action of the aggregated material into a generally single cellular material. However, holes 38 are preferably of the same size and shape as holes 28 of the first shear plate. Preferably, holes 28 and 38 on adjacent shear plates, e.g. 26 and 36, do not align. For the square matrix hole arrangement described below, a 45° rotation of one shear plate relative to the other appears to maximize the shear effect. It has been found advantageous to have a greater number of holes in the interior shear plates relative to the first exterior shear plate. Such a configuration prevents "spurting" of the cytological material to the top of body 10. Currently, it is preferred to have 24 holes 28 on first shear plate 26 and four holes 38 in second shear plate 36, first shear plate 26 having 24 holes 28 in a 5×5 square matrix, with the central hole in the matrix being absent, and second shear plate 36 having four holes 38 in a 2×2 square matrix. Although shear plates 26 and 36 may be spaced at any effective distance, it is currently preferred to space the plates at a distance of about 0.24 inches (0.61 cm) apart.

Shear plate member 34 is designed to fit snugly within the opening 35 of first shear plate member 24 with annular ring 31 holding second shear plate member 34 in place in opening 35. The positioning of second shear plate 36 is shown in FIG. 7 at the bottommost location of member 34. However, the invention also encompasses shear plate 36 placed at a location anywhere along the longitudinal axis of member 34. The exact positioning of the first and second shear plates relative to each other is not critical. However, the plates should be generally parallel to each other and adjacent or proximate to each other such that a large percentage of the cytological material which passes through second shear plate 36 also passes through first shear plate 26 before entering chamber 11. The plates are typically placed as close as possible without impeding the flow of the cytological material therethrough.

It will be apparent to the ordinary artisan that any number of shear plates (limited by geometries and spatial considerations readily determinable by one skilled in the art) may be used in the device 1. The invention is not limited to the two shear plate members shown.

As an additional embodiment of the invention, the device may be provided with a mesh screen which spans the entire cross-section of the hollow body. The mesh is of a size to ensure that particles of certain size enter the chamber 11. If one shear plate is used in the invention, the mesh screen is preferably placed above the shear plate within chamber 11. If two or more shear plates are used, the mesh screen is preferably placed between the first and second shear plates. The mesh screen provides two important functions: (i) assisting in the disaggregation of the cell clumps and (ii) preventing material above a certain size to enter chamber 11. Preferably, mesh size is from about 80 to about 100 microns, but exact mesh size is a matter of design choice.

Figure 10:
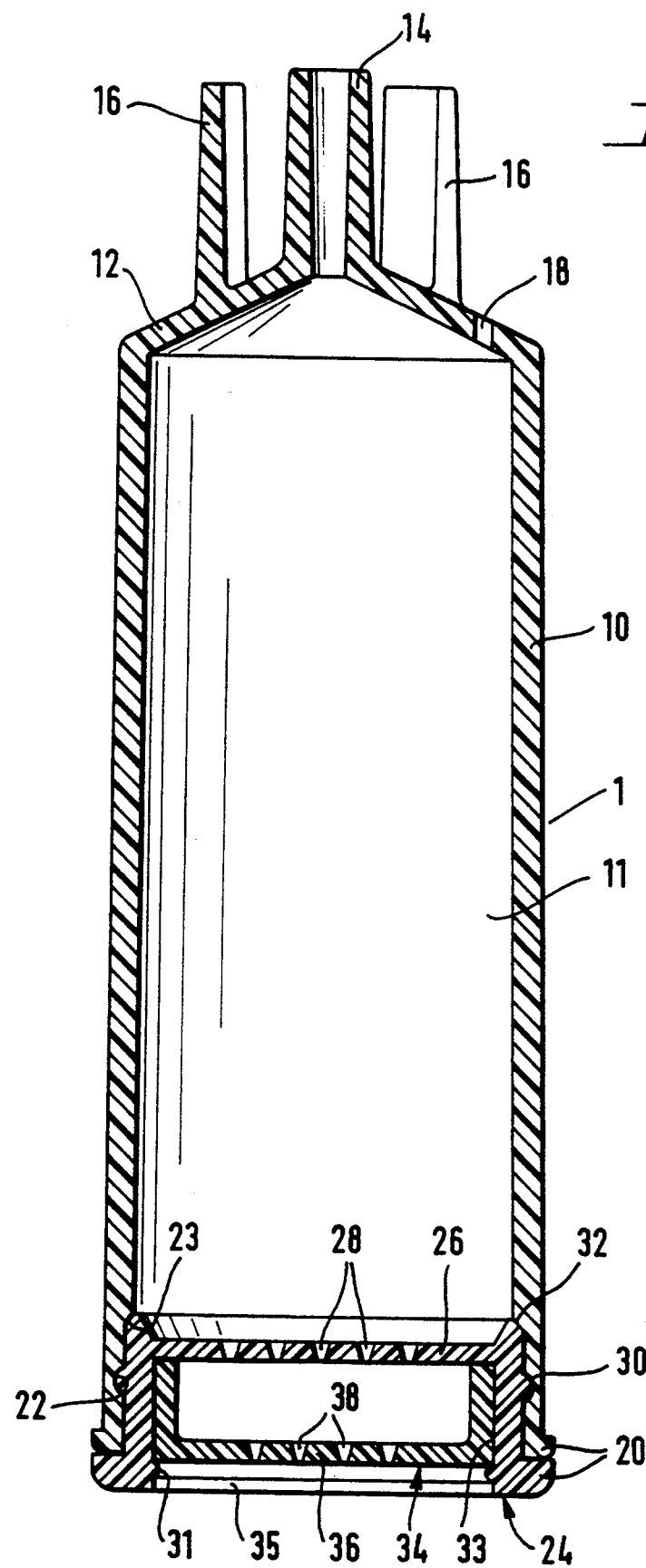
FIG. 10 shows a cross-section of a preferred embodiment of the device 1 when completely assembled.

FIG. 10 shows a cross-section of a preferred embodiment of the device 1 when completely assembled.

Figure 11:
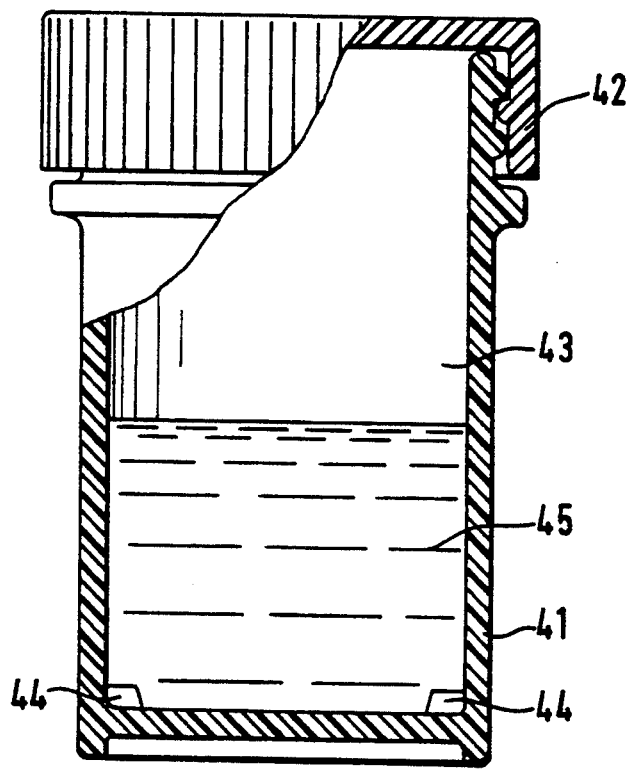
FIG. 11 shows a partially cross-sectioned side view of a sample vial suitable for use with the subject invention.

FIG. 11 shows a side perspective view of the sample vial 41 as it would be received from a doctor's office or clinic. When received, sample vial 41 contains a sample containing fluid 45 and a volume of air 43 contained by cap 42. To begin the desegregation, a technician removes cap 42 from sample vial 41, so as to ready the sample for disaggregation.

Figure 12:
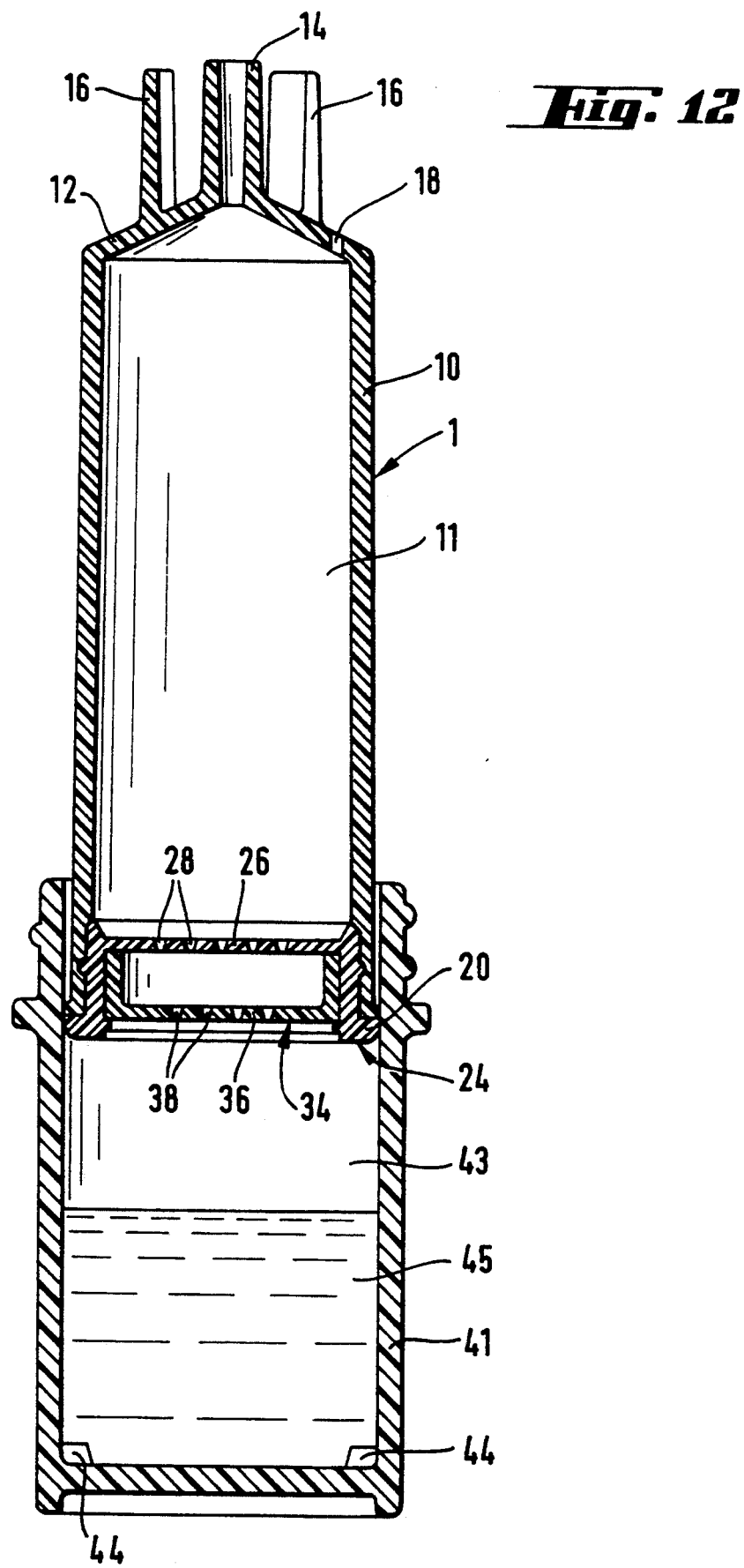
FIG. 12 illustrates a cross-sectional view of the device of FIG. 10 partially inserted into a sample vial.

FIG. 12 shows a cross-sectional view of device 1 being inserted into sample vial 41. As shown, device 1 is slidably inserted into sample vial 41 so that air 43, followed by sample containing fluid 45, is forced through second sheer plate 36, followed by first sheer plate 26, until the disaggregated material enters chamber 11.

Figure 13:
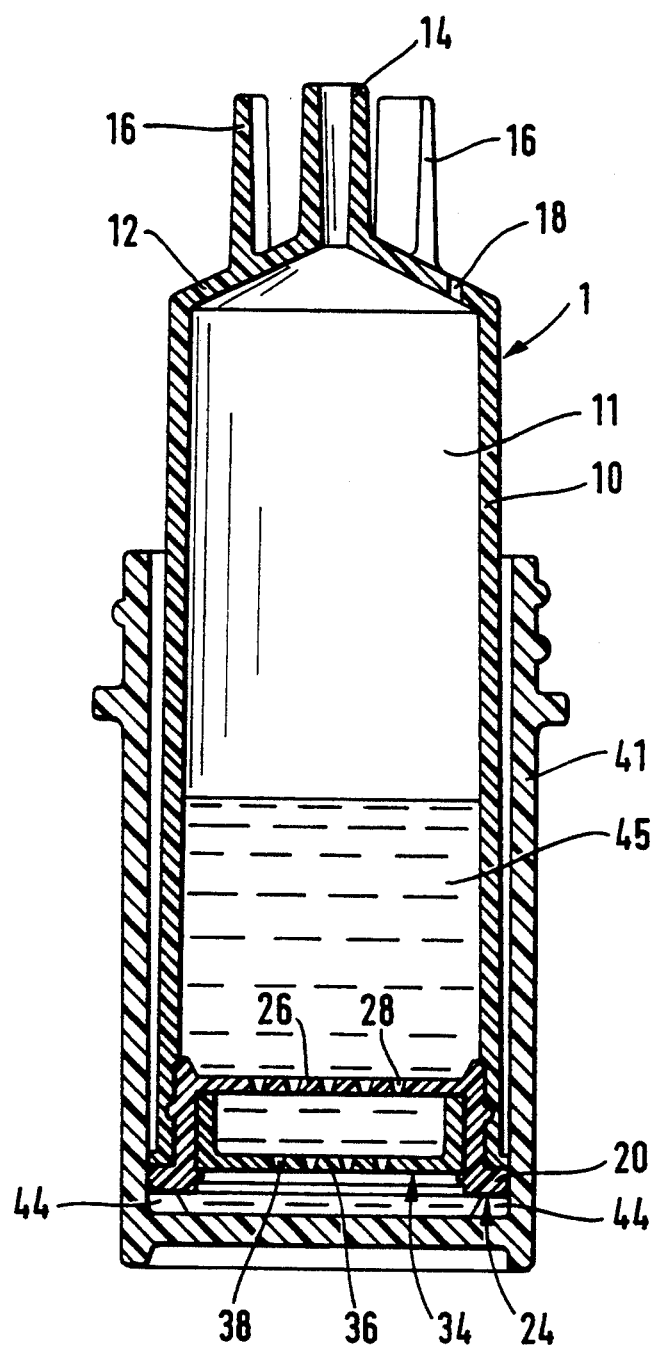
FIG. 13 shows the same view as FIG. 12 where the device is fully inserted into the vial.

FIG. 13 illustrates device 1 completely inserted into sample vial 41. Sample fluid 45 (now disaggregated cytological material) is now within chamber 11. One preferred feature of the design is that device 1 does not contact the bottom of sample vial 41, because shoulder 44 (see FIG. 13) prevents device 1 from reaching the bottom of vial 41. This reserves an amount of fluid (typically about 2 mL) in the event the disaggregated material is wasted, thus allowing a second sample to be generated if need be. Withdrawal of device 1 from sample vial 41 causes a suction effect causing the sample fluid 45 to again traverse first sheer plate 26 and then second sheer plate 36 to reenter sample vial 41. By repeating this plunging activity, sample fluid 45 is volleyed between chamber 11 and sample vial 41 to further disaggregate the cytological material.

Once the disaggregated cytological material is contained within chamber 11, the combined device 1 and sample vial 41 maybe inverted as a single unit to allow the sample fluid 45 to drain via connector 14. As stated above, connector 14 is preferably coupled to a curved tube which is configured to allow gentle layering of the cell suspension onto a density gradient.

The above-described device can be manufactured from any type of material. In a preferred embodiment, the majority device is manufactured using low density polyethylene, and the shear plate is formed from polypropylene or other similar material. As apparent, the choice of material can be readily determined by a skilled artisan.

Having described the structure of the device, its use will now be described. After receiving a sample vial containing cytological material in physiological saline solution from a clinic, the laboratory technician inserts device 1 directly into the sample vial and exerts a downward force on the device to force cytological material upward through the shear plates. Downward movement of the device continues until the device has reached the bottom limit of movement in the vial. After a first passage, the technician may, at his or her option depending on the quality of disaggregation required, withdraw the device from the vial by pulling on it. The pulling action creates a vacuum-effect within the sample vial and draws the cytological material from the chamber 11 through the shear plates and back into the vial. The device is then ready to again be forced into the fluid to disaggregate the cells clumps. This procedure may be repeated as many times as is necessary to achieve the required degree of disaggregation.

Figure 14:
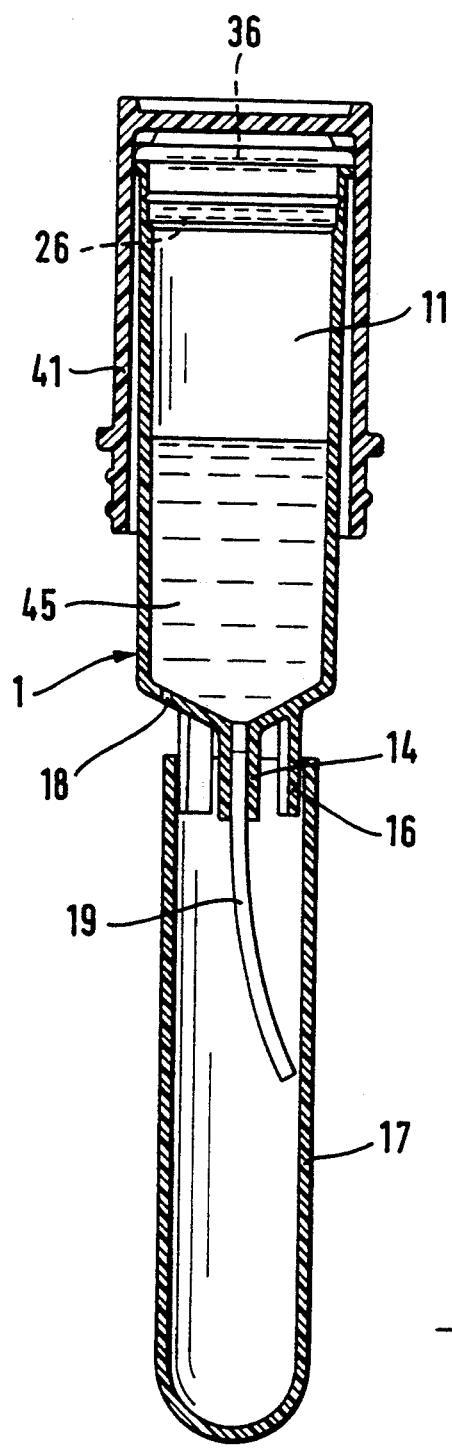
FIG. 14 shows a side cross-sectional view which illustrates draining of disaggregated suspension from the subject device into a tube/via a hose.

Once the desired degree of cell clump disaggregation has been achieved, the cell suspension is then ready for subsequent processing. In a preferred embodiment, wherein a hose or tube is connected to the top end portion of the device as described above, and as shown in the Figures, the device may be removably secured through securing means 16, shown in FIG. 2, to a receiving receptacle, e.g., test tube, centrifuge tube 17 or the like (see FIG. 14), then inverted. The inverted device allows the cell suspension occupying chamber area 11 of cylindrical body 10 to drain directly into the receptacle for subsequent processing.

It will become apparent that other variations on the invention may be made without departing from the scope and spirit of the invention, defined in the appended claims.

What is claimed is:

1. The combination of a device for disaggregating cytological material contained within a sample vial, and a tube for receiving dissaggregated cytological material from the device, which comprises:
   (a) the device comprising:
      (i) an elongated hollow body configured and dimensioned to be slidably inserted into the sample vial, the body having a top end, a bottom end and sides;
      (ii) sealing means for forming a liquid-impervious seal between the sample vial and the body when the body is inserted into the sample vial;

(iii) a shear plate disposed across the bottom end of the body, the shear plate defining a plurality of holes of predetermined size effective to disaggregate the cytological material and to permit the disaggregated cytological material to traverse the shear plate and enter the body when the body is inserted into the sample vial; and (iv) a curved hose having a proximate end and a distal end, the proximate end being coupled to the top end of the body so that the disaggregated cytological material is permitted to flow from the top end of the body into and through the hose; and (b) the tube having an open end, a closed end, an interior surface and an exterior surface, the tube at its open end being configured and dimensioned to be securable to the top end of the body;

such that when the tube is secured to the body, the hose is configured and dimensioned so that its distal end contacts the interior surface of the tube.

2. The combination of claim 1, wherein the shear plate is positioned substantially perpendicular to the longitudinal axis of the body.

3. The combination of claim 1, wherein the device comprises two shear plates.

4. The combination of claim 3, wherein the two shear plates are parallel.

5. The combination of claim 4, wherein the holes defined by the two shear plates are not aligned.

6. The combination of claim 1, wherein the device further comprises a mesh screen located adjacent to the shear plate, the mesh screen being configured and dimensioned to prevent cytological material larger than a predetermined size from entering the body.

7. The combination of claim 1, wherein the device further comprises securing means for securing the top end of the body to the open end of the tube.

8. The combination of claim 7, wherein the securing means comprise a flange.

9. The combination of claim 8, wherein the flange is configured and dimensioned to be insertable into the open end of the tube and to contact the interior surface of the tube.

10. The combination of claim 1, wherein the sealing means comprise a protrusion extending from the sides of the body.

* * * * *